United States Patent [19]

Iwata

[11] Patent Number: 5,684,248
[45] Date of Patent: Nov. 4, 1997

[54] DEVICE FOR DETERMINING THE DEGREE OF DETERIORATION OF A CATALYST

[75] Inventor: Yoichi Iwata, Yokohama, Japan

[73] Assignee: Toyota Jidosha Kabushiki Kaisha, Aichi, Japan

[21] Appl. No.: 715,398

[22] Filed: Sep. 18, 1996

[30] Foreign Application Priority Data

Sep. 20, 1995 [JP] Japan .................. 7-241729

[51] Int. Cl.$^6$ .................. F01N 3/20; G01N 27/409; F02D 41/22
[52] U.S. Cl. .................. 73/118.1; 73/23.32; 73/116; 60/277; 364/431.051; 364/431.062; 340/438
[58] Field of Search .................. 73/23.31, 23.32, 73/116, 117.2, 117.3, 118.1, 118.2; 60/277; 364/431.03, 431.04, 431.051, 431.062; 340/438, 439

[56] References Cited

U.S. PATENT DOCUMENTS

| | | | |
|---|---|---|---|
| 5,228,335 | 7/1993 | Clemmens et al. | 73/118.1 |
| 5,303,580 | 4/1994 | Schneider et al. | 73/118.1 |
| 5,365,216 | 11/1994 | Kotwicki et al. | 73/118.2 |
| 5,408,215 | 4/1995 | Hamburg | 73/118.1 |
| 5,428,956 | 7/1995 | Maus et al. | 73/118.1 |
| 5,431,011 | 7/1995 | Casarella et al. | 73/118.1 |

FOREIGN PATENT DOCUMENTS

| | | |
|---|---|---|
| A-4-303754 | 10/1992 | Japan . |
| A-5-10181 | 1/1993 | Japan . |
| A-5-18231 | 1/1993 | Japan . |

*Primary Examiner*—George M. Dombroske
*Attorney, Agent, or Firm*—Oliff & Berridge

[57] ABSTRACT

A device for determining the degree of deterioration of catalyst of a catalytic converter arranged in an internal combustion engine exhaust system is disclosed. The device comprises an $O_2$ sensor which is arranged in the internal combustion engine exhaust system downstream of the catalytic converter. The $O_2$ sensor has the low oxidization and deoxidization ability on the detection surface thereof. The device determines the degree of deterioration of the catalyst by comparing a value in connection with an extra $O_2$ concentration on the basis of a current output of the $O_2$ sensor in the exhaust gas at a predetermined air-fuel ratio with a basic value.

6 Claims, 8 Drawing Sheets

DEVICE FOR DETERMINING THE DEGREE OF DETERIORATION OF A CATALYST

BACKGROUND OF THE INVENTION

1. Field of the Invention

The present invention relates to a device for determining the degree of deterioration of a catalyst.

2. Description of the Related Art

A catalyst is usually arranged in an exhaust passage to purify the exhaust gas. Once the catalyst deteriorates excessively, the catalyst cannot purify the exhaust gas sufficiently. Accordingly, it is necessary to determine that the degree of deterioration of the catalyst is excessive, to inform the driver about this, and to urge the driver to exchange the catalyst for a new one.

The exchange involves much cost and much time and these must be minimized. Accordingly, it is necessary to determine the degree of deterioration of a catalyst precisely. Japanese Unexamined Patent Publication No. 4-303754 discloses a device for determining the degree of deterioration of a catalyst. The device has a first $O_2$ sensor arranged upstream of the catalyst and a second $O_2$ sensor arranged downstream $O_2$ the catalyst, and determines the current $O_2$ storage ability by comparing an upstream $O_2$ concentration detected by the first $O_2$ sensor with a downstream $O_2$ concentration detected by the second $O_2$ sensor, and assumes a current degree of deterioration of the catalyst from the current $O_2$ storage ability which drops according to the deterioration of the catalyst. The document No. 4-303754 also discloses that $H_2$ resistant means, i.e., a protection coat is provided with these $O_2$ sensors, because $H_2$ in the exhaust gas influences outputs of these $O_2$ sensors.

Recently, an air-fuel ratio control which can maintain a stoichiometric air-fuel ratio has been suggested. In this case, it is unnecessary that an $O_2$ storage ability is provided in the catalyst. The above-mentioned device cannot detect the degree of deterioration of a catalyst in the case that the catalyst does not have a $O_2$ storage ability or the $O_2$ storage ability of the catalyst does not deteriorate.

SUMMARY OF THE INVENTION

Therefore, an object of the present invention is to provide a device for determining the degree of deterioration of a catalyst, capable of determining the degree of deterioration of the catalyst independently of the $O_2$ storage ability thereof.

According to the present invention, there is provided a device for determining the degree of deterioration of catalyst of a catalytic converter, arranged in an internal combustion engine exhaust system, comprising: an $O_2$ sensor which is arranged in the internal combustion engine exhaust system downstream of the catalytic converter, which has a low oxidization and deoxidization ability on the detection surface thereof; and determining means for determining the degree of deterioration of the catalyst by comparing a value in connection with an extra $O_2$ concentration, on the basis of a current output of the $O_2$ sensor in exhaust gas of a predetermined air-fuel ratio, with a basic value.

According to the present invention, there is provided another device for determining the degree of deterioration of a catalyst in a catalytic converter arranged in an internal combustion engine exhaust system, comprising: a step-output type $O_2$ sensor arranged in the internal combustion engine exhaust system downstream of the catalytic converter, which has a low oxidization and deoxidization ability; control means for controlling the air-fuel ratio of the mixture rich at a predetermined waveform during a predetermined period; and determining means for determining the degree of deterioration of the catalyst by comparing a period during which the $O_2$ sensor represents that the exhaust gas is rich with a basic period.

The present invention will be more fully understood from the description of preferred embodiments of the invention set forth below, together with the accompanying drawings.

DESCRIPTION OF THE PREFERRED EMBODIMENTS

Figure 1:
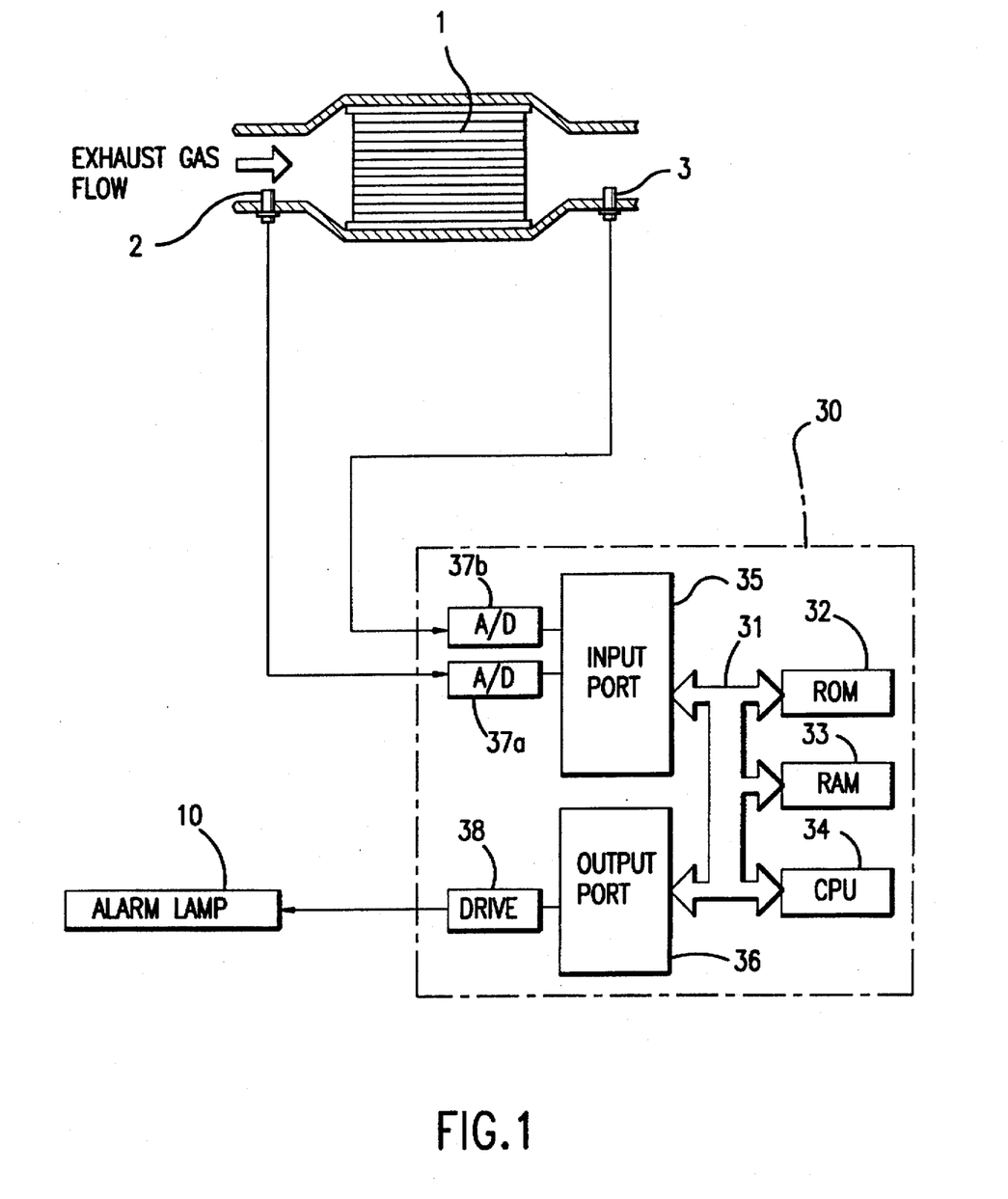
FIG. 1 is a sectional view of a part of an internal combustion engine exhaust system with a device for determining the degree of deterioration of a catalyst of the first embodiment.

FIG. 1 is a sectional view of a part of an internal combustion engine exhaust system with a device for determining the degree of deterioration of a catalyst of a first embodiment according to the present invention. Referring to FIG. 1, reference numeral 1 designates a catalytic converter which purifies the exhaust gas. The upstream side of the catalytic converter 1 is connected to the engine body (not shown). On the other hand, the downstream side thereof is opened to the atmosphere, via a muffler (not shown). Reference numeral 2 designates a first $O_2$ sensor arranged upstream of the catalytic converter 1. The first $O_2$ sensor 2 is a linear-output type which can detect an extra $O_2$ concentration in exhaust gas flowing into the catalytic converter 1. When the exhaust gas is on the lean side, the output of the linear-output type $O_2$ sensor 2 becomes a positive value according to the degree of leanness of the exhaust gas. When the exhaust gas is stoichiometric, the output of the linear-output type $O_2$ sensor 2 becomes [0]. When the exhaust gas is on the rich side, an output of the linear-output type $O_2$ sensor 2 becomes a negative value according to the degree of richness of the exhaust gas.

Reference numeral 3 designates a second $O_2$ sensor arranged downstream of the catalytic converter 1. The second $O_2$ sensor 2 is the linear-output type which can detect an extra $O_2$ concentration in exhaust gas flowing out from the catalytic converter 1. The detection surface of the second $O_2$ sensor undergoes a poison treatment, for example, a lead treatment or the like.

Figure 2A:
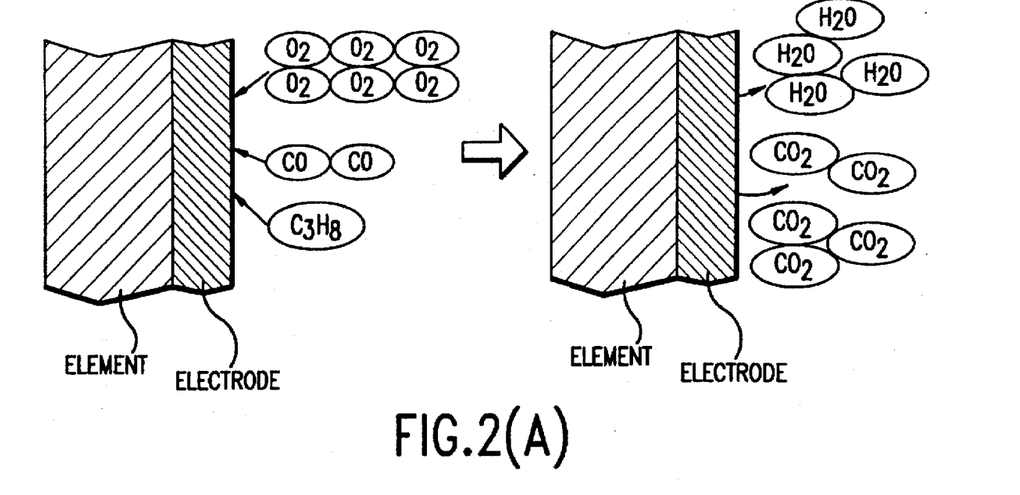
FIG. 2(A) is a explanatory view of the oxidization reaction of the first $O_2$ sensor.

The first $O_2$ sensor 2, i.e., the usual $O_2$ sensor, deoxidizes $NO_x$ in the exhaust gas and oxidizes CO and HC therein by $O_2$ which is generated by the deoxidization and which is contained therein, on the detection surface of the sensor, i.e., the surface of the electrode of the sensor element, as a three-way catalyst. As a result, the first $O_2$ sensor 2 detects an extra $O_2$ concentration in the exhaust gas. As shown in FIG. 2(A), in the stoichiometric exhaust gas, the oxidization is carried out so that the extra $O_2$ concentration therein becomes [0].

Figure 2B:
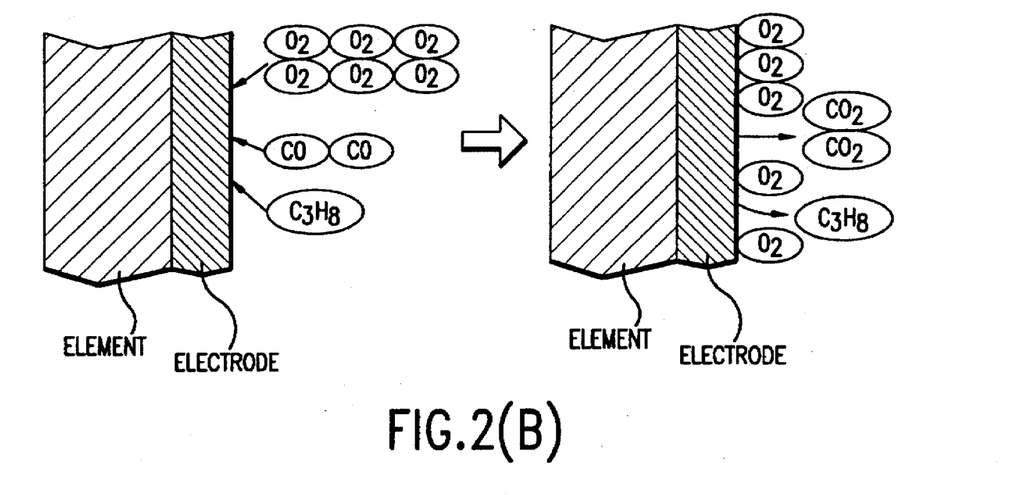
FIG. 2(B) is a explanatory view of the oxidization reaction of the second $O_2$ sensor.

However, in the second $O_2$ sensor 3, the detection surface thereof undergoes the poison treatment so that the oxidization ability of HC, which is hard to oxidize in comparison with CO, drops. Therefore, as shown in FIG. 2(B), in the stoichiometric exhaust gas, the second $O_2$ sensor 3 cannot oxidize a part of HC which arrives at the detection surface and thus an amount of $O_2$, according to an amount of HC which is not oxidized, remains on the detection surface. The second $O_2$ sensor 3 detects the amount of $O_2$, as extra $O_2$ in the exhaust gas.

The catalytic converter 1 gradually deteriorates with the use thereof. Once the degree of deterioration of the catalytic converter 1 becomes excessive, the purification ability thereof becomes very low so that the exchange thereof is necessary. Reference numeral 30 is a device which determines the degree of deterioration of the catalyst to determine the time of such an exchange.

The device 30 is an electronic control unit (ECU). The ECU 30 is constructed as a digital computer and includes a ROM (read only memory) 32, a RAM (random access memory) 33, a CPU (microprocessor, etc.) 34, an input port 35, and an output port 36, which are interconnected by a bidirectional bus 31. The output voltage of the first $O_2$ sensor 2 is input into the input port 35 via an AD converter 37a. The output voltage of the second $O_2$ sensor 3 is input into the input port 35 via an AD converter 37b. The output port 36 is connected through a drive circuit 38 to an alarm lamp 10 showing that the degree of deterioration of the catalytic converter 1 has become excessive.

In the engine with the device for determining the degree of deterioration of a catalyst according to the present invention, the control of an amount of fuel injected is carried out by the usual feed-back air-fuel ratio control which can maintain a stoichiometric air-fuel ratio, except for predetermined engine operating conditions.

Figure 3:
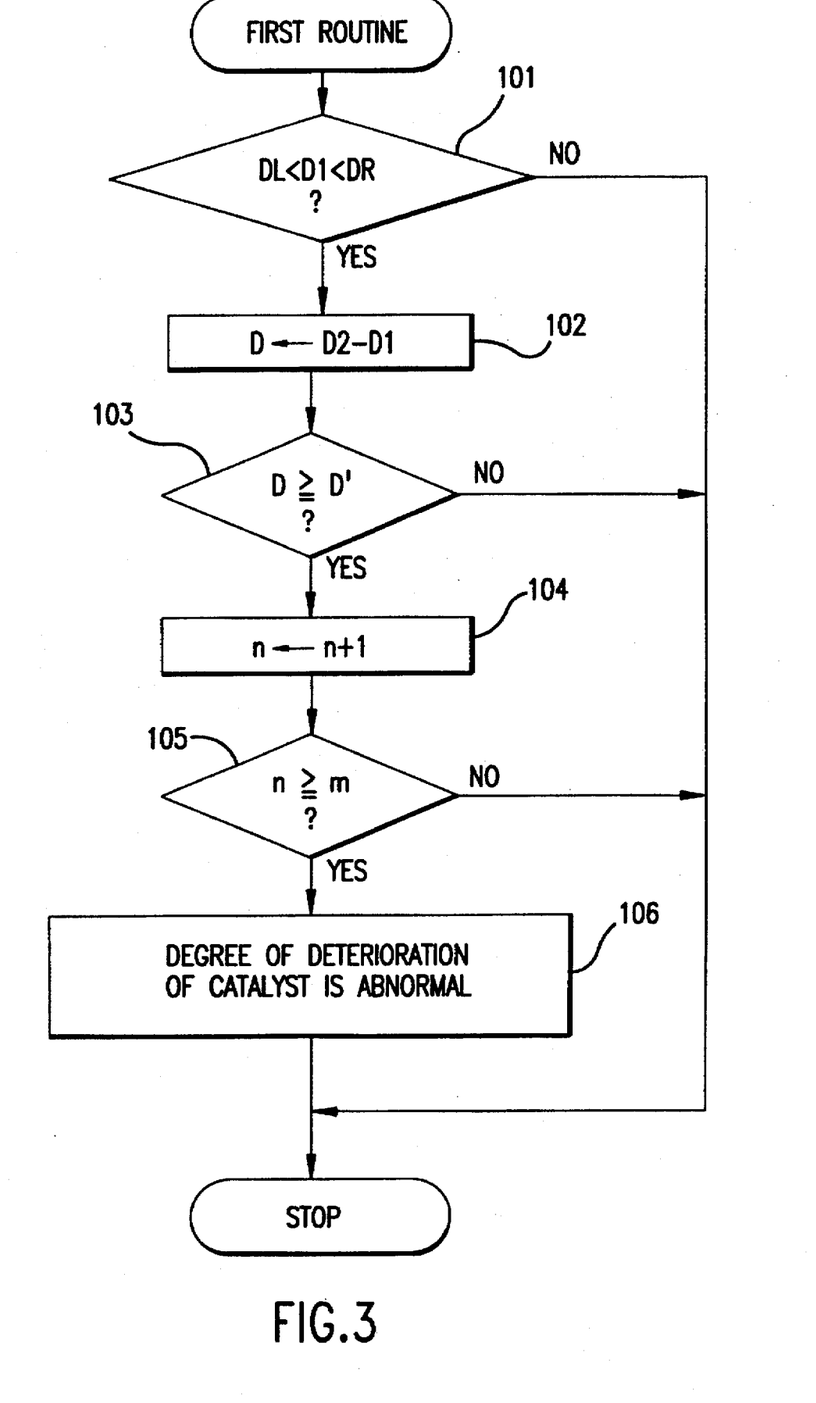
FIG. 3 is a first routine for determining the degree of deterioration of a catalyst.

FIG. 3 shows a first routine for determining the degree of deterioration of the catalytic converter 1. The routine is started simultaneously with the engine starting and is repeated at every predetermined period. First, at step 101, it is determined if the current output [D1] of the first $O_2$ sensor 2 is within a predetermined range [DL-DR], when the result is negative, the routine is stopped.

On the other hand, when the result at step 101 is positive, the routine goes to step 102 and a difference [D] between the current output [D2] of the second $O_2$ sensor 3 and the current output [D1] of the first $O_2$ sensor 2 is calculated. The three-way catalytic converter 1 deoxidizes $NO_x$ and oxidizes CO and HC so that these three harmful materials in the exhaust gas are converted into harmless materials, as $CO_2$, $H_2O$, and Accordingly, when the catalytic converter 1 does not deteriorate and functions sufficiently, in the stoichiometric exhaust gas, the HC, CO, $O_2$, and $NO_x$ concentrations downstream of the catalytic converter 1 are equally very much lower than those upstream thereof.

As above-mentioned, the oxidization ability of HC of the second $O_2$ sensor 3 drops so that the second $O_2$ sensor 3 detects an extra $O_2$ concentration on the basis of the amount of $O_2$ according to an amount of HC which is not oxidized on the detection surface. When the catalytic converter 1 does not deteriorate, the HC concentration in the exhaust gas downstream thereof is very low so that an amount of HC which is not oxidized on the detection surface of the second $O_2$ sensor 2 is very small. Accordingly, an extra $O_2$ concentration detected by the second $O_2$ sensor 3 at this time is nearly [0]. On the other hand, according to the deterioration of the catalytic converter 1, the HC, CO, $O_2$, and $NO_x$ concentrations downstream of the catalytic converter 1 become close to those upstream thereof, so that an extra $O_2$ concentration detected by the second $O_2$ sensor 3 becomes high.

In the stoichiometric air-fuel mixture, if some injected fuel, at a given rate, is discharged from the engine cylinder, the HC concentration upstream of the catalytic converter 1 is constant as far as the air-fuel ratio is stoichiometric. The first $O_2$ sensor 2 has a high oxidization ability on the detection surface to oxidize almost all the HC and CO which arrive to the detection surface. Accordingly, an extra $O_2$ concentration detected by the first $O_2$ sensor 2 arranged upstream of the catalytic converter 1 is always [0] as shown by a dotted line in FIG. 4, independent of the degree of deterioration of the catalyst.

Figure 4:
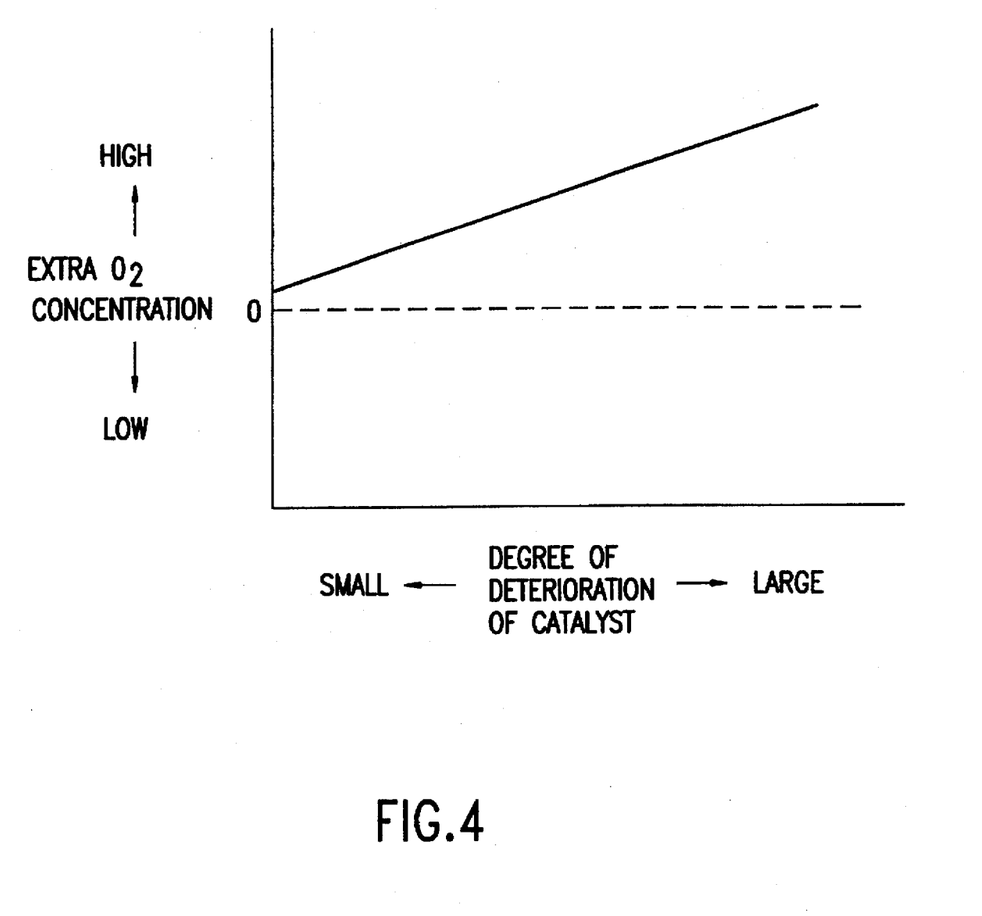
FIG. 4 represents two graphs which show extra $O_2$ concentrations detected by the first and second $O_2$ sensors against the degree of deterioration of the catalyst.

On the other hand, as shown by a solid line in FIG. 4, the larger the degree of deterioration of the catalyst is, the higher an extra $O_2$ concentration detected by the second $O_2$ sensor 3 becomes, As a result, the larger the degree of deterioration of the catalyst is, the larger the difference [D] calculated at step 102 becomes and the difference [D] represents the degree of deterioration of the catalyst. Therefore, at step 103, it is determined if the difference [D] is equal to or larger than a predetermined value [D']. When the result is negative, the routine is stopped as the degree of deterioration of the catalyst is relative small. When the result at step 103 is positive, the routine goes to step 104 and a count value [n] is increased by [1]. The count value is reset [0] when the engine is stopped. Next, at step 105, it is determined if the count value [n] is equal to or larger than a predetermined value [m]. When the result is negative, the routine is stopped. When the result at step 105 is positive, the routine goes to step 106, and it is determined that the degree of deterioration of the catalyst is abnormal and this is informed to the driver by the alarm lamp 10.

Figure 5:
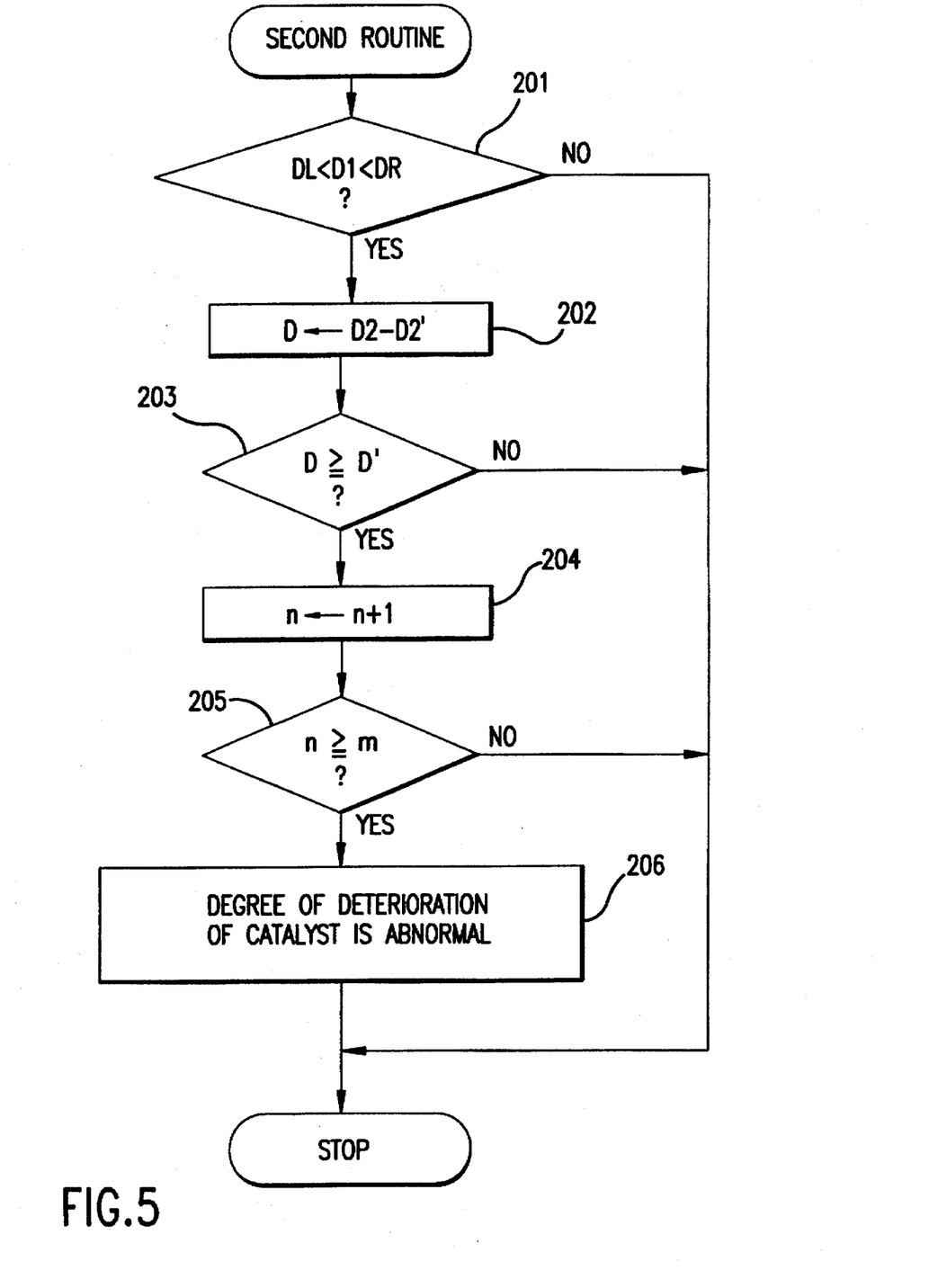
FIG. 5 is a second routine for determining the degree of deterioration of a catalyst.

FIG. 5 shows a second routine for determining the degree of deterioration of the catalytic converter 1. Only the difference between the first and second routines is explained as follows. In the second routine, at step 202, the difference [D] between the current output [D2] of the second $O_2$ sensor 3 and the output [D2'] of the second $O_2$ sensor 3 when the three-way catalytic converter 1 was new and when the air-fuel ratio was stoichiometric, is calculated- As above-mentioned, the larger the degree of deterioration of the catalyst becomes, the larger the output of the second $O_2$ sensor 3 becomes. Accordingly, the degree of deterioration of the catalyst can be determined by comparing the current output of the second $O_2$ sensor 3 with a basic value. In the first routine, the current output of the first $O_2$ sensor when the air-fuel ratio is stoichiometric is used as the basic value.

On the other hand, in the second routine, the output [D2'] of the second $O_2$ sensor 3 when the catalytic converter 1 was new and when the air-fuel ratio was stoichiometric, is used as the basic value.

Figure 6:
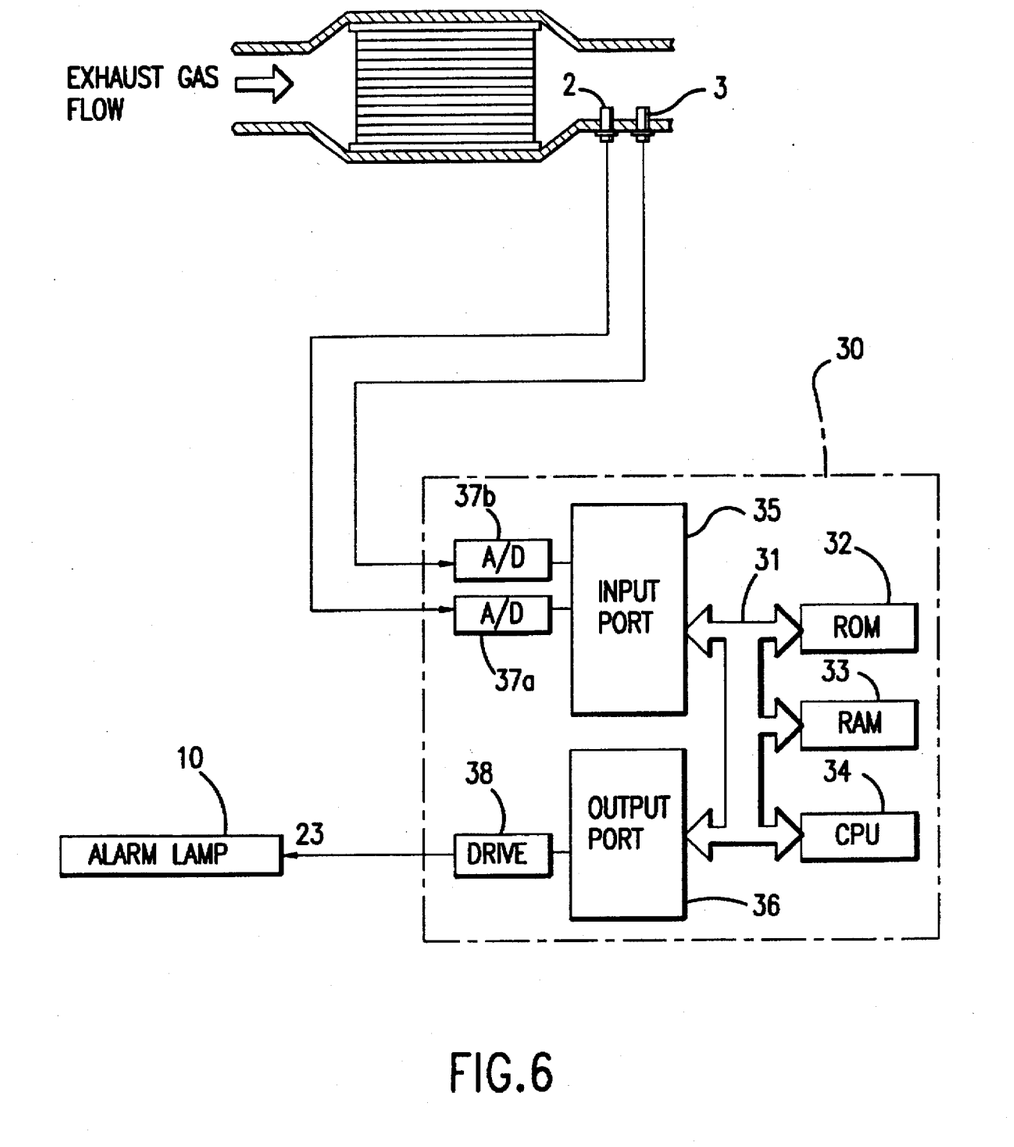
FIG. 6 is a sectional view of a part of an internal combustion engine exhaust system with a device for determining the degree of deterioration of a catalyst of the second embodiment.

FIG. 6 is a sectional view of a part of internal combustion engine exhaust system with a device for determining the degree of deterioration of a catalyst of a second embodiment according to the present invention. Only the difference between the first and second embodiments is explained as follows. In the second embodiment, the linear-output type first $O_2$ sensor 2 is arranged downstream of the catalytic converter 1 as same as the second $O_2$ sensor 3. In the second embodiment, the first routine shown in FIG. 3 is carried out for determining the degree of deterioration of the catalyst. The first $O_2$ sensor 2 has a high oxidization ability on the detection surface as above-mentioned, so that even if the degree of deterioration of the catalyst is large and the HC concentration remains high in the stoichiometric exhaust gas downstream of the catalytic converter 1, the first $O_2$ sensor 1 represents the stoichiometric exhaust gas, i.e., the extra $O_2$ concentration detected by the first $O_2$ sensor 2 becomes [0]. Accordingly, it is possible to determine the degree of deterioration of the catalyst by comparing the output [D2] of the second $O_2$ sensor with the output [D1] of the first $O_2$ sensor.

Figure 7:
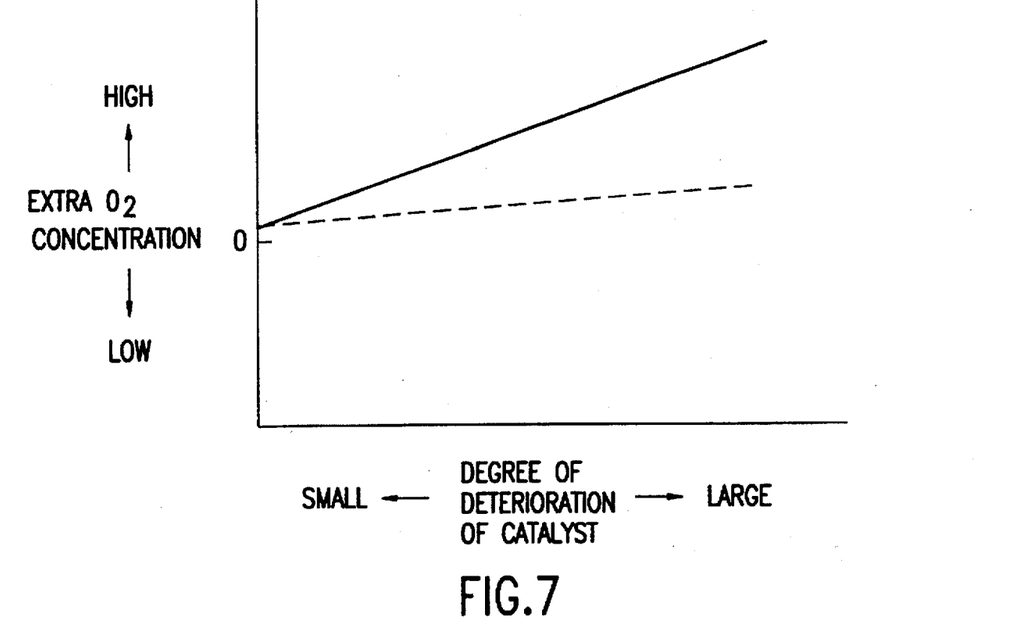
FIG. 7 represents two graphs which show extra $O_2$ concentrations detected by the first and second $O_2$ sensors against the degree of deterioration of the catalyst.

In the above embodiments, the first $O_2$ sensor 2 has a high oxidization ability on the detection surface. However, an $O_2$ sensor in which the oxidization ability is higher than in the second $O_2$ sensor 3 may be used as the first $O_2$ sensor 2. For example, when the first $O_2$ sensor 2 has a slightly low oxidization ability, the larger the degree of deterioration of the catalyst becomes and the higher the HC concentration in the stoichiometric exhaust gas downstream of the catalyst becomes, the higher the both of the extra $O_2$ concentrations detected by the first and second $O_2$ sensors 2, 3 become and the larger the difference between the two $O_2$ concentrations becomes, as shown in FIG. 7. Therefore, it is possible to determine the degree of deterioration of the catalyst on the basis of the difference.

In the above embodiments, the linear-output type $O_2$ sensor is used, as the first and second $O_2$ sensors. However, step-output type $O_2$ sensors may be used as the first and second $O_2$ sensors. A usual step-output type $O_2$ sensor has a characteristic in which the output changes suddenly when the extra $O_2$ concentration after the oxidization and deoxidization reactions on the detection surface is close to [0]. The step-output type $O_2$ sensor which has a high oxidization ability is arranged upstream or downstream of the catalytic converter 1, as the first $O_2$ sensor. Therefore, when the first $O_2$ sensor determines that the current exhaust gas is stoichiometric, it is possible to determine the degree of deterioration of catalyst by the degree of deviation of the output of the second $O_2$ sensor from the basic output corresponding to the stoichiometric exhaust gas.

Figure 8:
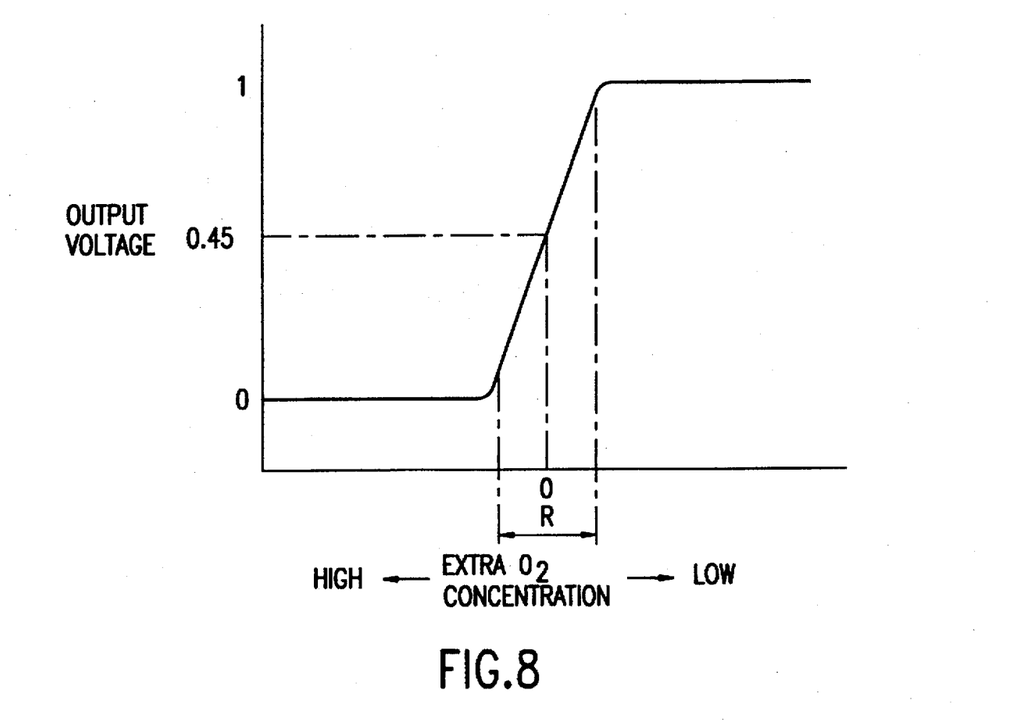
FIG. 8 represents a graph which shows an output voltage detected by a step-output type $O_2$ sensor against the degree of deterioration of the catalyst.

The output of the step-output type $O_2$ sensor changes suddenly when an extra $O_2$ concentration on the detection surface is close to [0], as shown in FIG. 8. During the sudden output change, the output is proportional to the extra $O_2$ concentration. Accordingly, for example, in case of the step-output type $O_2$ sensor of which the output varies from [0V] to [1V] when the exhaust gas varied from the lean side to the rich side, when the output thereof is [0.45V], the exhaust gas is stoichiometric.

The step-output type $O_2$ sensor in which the poison treatment is carried out on the detection surface thereof and of which the oxidization ability is lowered may be used as the second $O_2$ sensor. The step-output type $O_2$ sensor can be dealt with as the linear-output type $O_2$ sensor within a range [R] in FIG. 8, i.e., while the output of the step-output type $O_2$ sensor changes suddenly. The larger the degree of deterioration of the catalyst becomes, the smaller the output voltage of the step-output type $O_2$ sensor becomes. Accordingly, it is possible to determine the degree of deterioration of the catalyst in the basis of the output voltage thereof.

In the case of using the step-output type $O_2$ sensor as the second $O_2$ sensor, it is possible to determine the degree of deterioration of the catalyst only while the output thereof changes suddenly. Accordingly, a very large degree of deterioration of the catalyst cannot be determined. However, the catalytic converter 1 must be changed before the degree of deterioration of the catalyst becomes very large, and thus no problem occurs. If it is required to determine a very large degree of deterioration of the catalyst, an air-fuel ratio of the mixture is made rich until the output of the second $O_2$ sensor becomes [0.45V] and the degree of richness is detected by the linear-output type first $O_2$ sensor. It means that the larger the degree of richness is, the larger the degree of deterioration of catalyst is.

Figure 9:
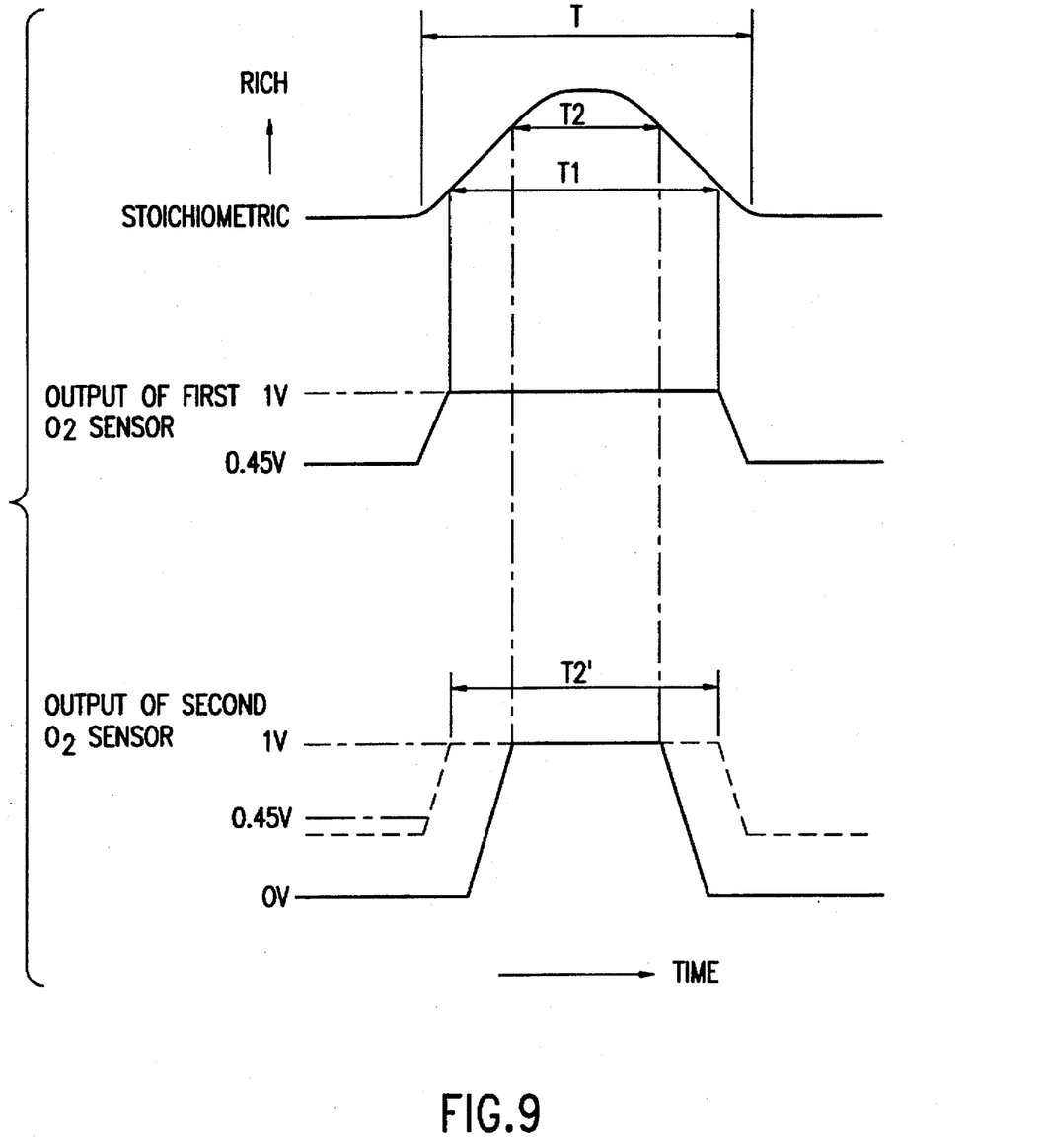
FIG. 9 represents time-charts which show variations in the air-fuel ratio of the mixture, the output of the first $O_2$ sensor, and the output of the second $O_2$ sensor.

When the step-output type $O_2$ sensor is used as the first $O_2$ sensor, as shown in time-charts of FIG. 9, the air-fuel ratio of the mixture is made rich at a predetermined waveform during a predetermined period [T]. The output of the second $O_2$ sensor varies gradually from a dotted line (when the catalytic converter 1 was new) to a solid line, according to the deterioration of the catalyst. Namely, the actual degree of rich of mixture when the second $O_2$ sensor represents the rich exhaust gas becomes large so that a period [T2] during which the second $O_2$ sensor represents the rich exhaust gas becomes short, according to the deterioration of the catalyst. Accordingly, it is possible to determine the degree of deterioration of the catalyst by comparing the period [T2] with the predetermined period [T], a period [T1] during which the first $O_2$ sensor represents the rich exhaust gas, or a period [T2'] during which the second $O_2$ sensor represents the rich exhaust gas when the catalytic converter 1 was new.

Although the invention has been described with reference to specific embodiments thereof, it should be apparent that numerous modifications can be made thereto by those skilled in the art, without departing from the basic concept and scope of the invention.

I claim:

1. A device for determining the degree of deterioration of catalyst of a catalytic converter arranged in an internal combustion engine exhaust system, said device comprising:

a first $O_2$ sensor, said first $O_2$ sensor producing a first voltage output proportional to an amount of $O_2$ present at a detection surface of said first sensor and said first sensor being arranged in said internal combustion engine exhaust system downstream of said catalytic converter, said first sensor having low oxidation and deoxidation ability on the detection surface thereof;

a second $O_2$ sensor being arranged in said internal combustion engine exhaust system upstream of said catalytic converter, said second sensor having a detection surface and producing a second voltage output proportional to an amount of $O_2$ present at the detection surface and having high oxidation and deoxidation ability on the detection surface thereof; and determining means for determining the degree of deterioration of said catalyst by comparing said first and second voltage outputs.

2. A device according to claim 1, wherein said first $O_2$ sensor has the low oxidization ability for hydro-carbon.

3. A device according to claim 1, wherein said first $O_2$ sensor is a linear-output type.

4. A device according to claim 1, wherein said first $O_2$ sensor is a step-output type.

5. A device for determining the degree of deterioration of catalyst of a catalytic converter arranged in an internal combustion engine exhaust system, said device comprising:

a first step-output type $O_2$ sensor, said first $O_2$ sensor producing a first voltage output proportional to an amount of $O_2$ present at said first sensor and said first sensor being arranged in said internal combustion engine exhaust system downstream of said catalytic converter, said first sensor having low oxidation and deoxidation ability;

control means for controlling the air-fuel ratio of exhaust gases in said exhaust system in accordance with a predetermined waveform during a predetermined period;

a second step-output type $O_2$ sensor producing a second voltage output proportional to an amount of $O_2$ present at said second sensor, and said second $O_2$ sensor being arranged in said internal combustion engine exhaust system upstream of said catalytic converter and having a high oxidation and deoxidation ability; and determining means for determining the degree of deterioration of said catalyst by comparing said first and second voltage outputs.

6. A device according 5, wherein said first $O_2$ sensor has the low oxidization ability for hydro-carbon.

* * * * *